US009399632B2

(12) United States Patent
Szeifert et al.

(10) Patent No.: US 9,399,632 B2
(45) Date of Patent: Jul. 26, 2016

(54) PROCESS FOR PRODUCING A SOLID OXIDIC MATERIAL

(71) Applicant: BASF SE, Ludwigshafen (DE)

(72) Inventors: Johann Martin Szeifert, Mannheim (DE); Michael Kutschera, Neustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/171,960

(22) Filed: Feb. 4, 2014

(65) Prior Publication Data

US 2014/0221671 A1 Aug. 7, 2014

Related U.S. Application Data

(60) Provisional application No. 61/760,677, filed on Feb. 5, 2013.

(51) Int. Cl.

| C07D 317/38 | (2006.01) |
|---|---|
| B01J 13/00 | (2006.01) |
| C04B 38/04 | (2006.01) |
| B01J 37/00 | (2006.01) |
| B01J 35/10 | (2006.01) |
| B01J 21/08 | (2006.01) |
| B01J 35/00 | (2006.01) |
| B01J 35/08 | (2006.01) |
| C04B 28/26 | (2006.01) |
| C04B 38/00 | (2006.01) |
| C04B 40/02 | (2006.01) |

(52) U.S. Cl.
CPC ........... *C07D 317/38* (2013.01); *B01J 13/0091* (2013.01); *C04B 38/04* (2013.01); *B01J 21/08* (2013.01); *B01J 35/0026* (2013.01); *B01J 35/08* (2013.01); *B01J 35/1019* (2013.01); *B01J 37/0045* (2013.01)

(58) Field of Classification Search
CPC ...... C07D 317/38; C07C 29/32; C07C 37/11; C04B 38/04; C04B 28/26; C04B 38/0067; C04B 40/0263; B01J 13/0091; B01J 37/0045; B01J 35/1019; B01J 21/08; B01J 35/0026; B01J 35/08
USPC .................................. 549/230; 568/763, 852
See application file for complete search history.

(56) References Cited

U.S. PATENT DOCUMENTS

| 2,249,767 A | 7/1941 | Kistler |
|---|---|---|
| 4,667,417 A | 5/1987 | Graser et al. |
| 5,122,291 A | 6/1992 | Wolff et al. |
| 5,409,683 A | 4/1995 | Tillotson et al. |
| 5,738,801 A | 4/1998 | Ziegler et al. |
| 6,475,561 B1 | 11/2002 | Schwertfeger |
| 6,516,537 B1 | 2/2003 | Teich et al. |
| 2005/0079337 A1 | 4/2005 | Hashida et al. |

FOREIGN PATENT DOCUMENTS

| DE | 196 16 263 A1 | 10/1997 |
|---|---|---|
| DE | 197 52 456 A1 | 5/1999 |
| DE | 198 10 565 A1 | 9/1999 |
| EP | 0171722 A2 | 2/1986 |
| EP | 0 396 076 A1 | 11/1990 |
| EP | 0 65 3377 A1 | 5/1995 |
| EP | 0 849 220 A1 | 6/1998 |
| WO | WO-95/06617 A1 | 3/1995 |

OTHER PUBLICATIONS

Luck, W.A.P., Intermolecular forces: an introduction to modern methods and results. Springer Verlag, 1991, Chapter IX, p. 217-249.*
Pierre, A.C., "Chemistry of aerogels and their applications." Chemical Reviews 102.11 (2002): 4243-4266.*
U.S. Appl. No. 61/760,678.
U.S. Appl. No. 61/760,677.
U.S. Appl. No. 61/760,679.
Yokogawa, H., et al., "Hydrophobic Silica Aerogels", Journal of Non-Crystalline Solids, vol. 186, (1995), pp. 23-29.
Roy, C., et al., "Assessment of scCO2 Techniques for Surface Modification of Micro- and Nanoparticles: Process Design Methodology Based on Solubility", J. of Supercritical Fluids, vol. 54, (2010), pp. 362-368.
Slostowski, C, et al., "Near- and Supercritical alcohols as Solvents and Surface Modifiers for the Continuous Synthesis of Cerium Oxide Nanoparticles", Langmuir, vol. 28, No. 48, (2012), pp. 16656-16663.

\* cited by examiner

*Primary Examiner* — Samantha Shterengarts
*Assistant Examiner* — Matt Mauro
(74) *Attorney, Agent, or Firm* — Drinker Biddle & Reath LLP

(57) ABSTRACT

The present invention relates to a process for producing a porous solid oxidic material from a hydrogel of the oxidic material and to the porous solid oxidic material as such.

17 Claims, No Drawings

PROCESS FOR PRODUCING A SOLID OXIDIC MATERIAL

CROSS-REFERENCE TO RELATED APPLICATIONS

This application claims the benefit of U.S. Provisional Application 61/760,677, filed Feb. 5, 2013, which is incorporated herein by reference.

The present invention relates to a process for producing a porous solid oxidic material from a hydrogel of the oxidic material and to the porous solid oxidic material as such.

Porous oxidic materials are of interest for numerous applications, for example as adsorbents, fillers, release agents, thickeners, dispersing aids, free-flow aids, defoamers, matting additives, active ingredient carriers and/or catalyst supports. Among the porous solid oxidic materials, the class of aerogels is of particular significance. Aerogels are porous solid oxidic materials generally consisting of silicon oxides, i.e. silica, or metal oxides. Aerogels, especially aerogels of silica, are of excellent suitability as thermal insulation material because their thermal conductivity is only low, or as support material for catalysts because their specific surface area is high. Further fields of use of aerogels are in the fields of plastics, for example natural and synthetic rubbers, adhesives, paints, coatings, pharmaceuticals, cosmetics, the paper, textile, mineral oil and fiber industry, and glass technology, pyrotechnology and foundry technology, where aerogels find various uses as dispersing aids, reinforcers, free-flow aids, antisettling agents, fillers, defoamers, active ingredient carriers, matting additives and/or absorbents.

The production of porous solid oxidic materials, for example aerogels, is generally possible by dewatering hydrated forms of the oxidic materials, called hydrogels. However, this dewatering operation is associated with a number of problems. The removal of the water from the hydrogel by simply heating can lead to the collapse of the hydrogel or to the crystallization of the oxidic material, such that the resulting oxidic material is compact and has only low porosity, if any. In order to avoid these problems, the hydrogel can be generated and immediately dried in situ, for example by spraying waterglass and mineral acid in a spray drying apparatus.

It is known that the water present in the hydrogel can be displaced by treatment with a lower-boiling water-soluble liquid, for example volatile alkanols such as methanol, ethanol or isopropanol, and that the dewatered material obtained (called an alcogel when alcohols are used) can be dried under supercritical conditions (see, for example, U.S. Pat. No. 2,249,767). EP 171722 discloses performing such a supercritical drying operation in $CO_2$.

For many applications, especially in the case of use as thermal insulation material, the absorption of water into the porous solid oxidic material is undesirable, since the material ages in the process and its advantageous properties are lost. The drying of the organogel in the presence of alcohols does lead to a certain hydrophobization, since the alcohol molecules, through their OH groups, can enter into a chemical bond with the surface of the oxidic material. However, the hydrophobization achieved is low and is not stable in the long term.

Known hydrophobizing reagents include further compounds, for example organosilicon compounds, with which the dried hydrogel is treated in the gas phase or which may also already be present in the course of precipitation, further intermediate process steps or supercritical drying. The coverage of the surface with hydrophobic compounds is supposed to prevent the porous solid oxidic material from absorbing water again. However, the reagents used for hydrophobization are costly, and the long-term stability of the hydrophobization achieved is likewise unsatisfactory.

WO 95/06617 describes a process for producing hydrophobized silica aerogels having improved properties, which comprises the reaction of a waterglass solution with an acid, washing the hydrogel formed with water to remove ionic constituents, treatment of the hydrogel with an alcohol, especially isopropanol, and supercritical drying of the resulting alcogel in the presence of the alcohol. However, the hydrophobization achieved, more particularly the long-term stability thereof, is likewise unsatisfactory.

The porous solid oxidic materials produced in accordance with the prior art thus have the disadvantage that, in spite of a hydrophobized surface, they have a tendency to absorb water and therefore do not have long-term stability. It was therefore an object of the invention to provide a process which overcomes these disadvantages of the prior art.

It has now been found that, surprisingly, these disadvantages can be overcome if the removal of the water is accomplished by treating a hydrogel of an oxidic material with a water-miscible organic liquid and then drying the organogel obtained under supercritical conditions in the presence of at least one polyfunctional compound C having at least two reactive functionalities F which can react to form a bond with the atoms of the solid oxidic material, the at least one polyfunctional compound C being used in the supercritical drying operation as a solution of the compound C in at least one organic solvent S' having 0 or 1 reactive functionality F, and/or as a mixture with $CO_2$, the reactive functionalitites F being selected from hydroxyl groups, especially carbon-bonded hydroxyl groups, carboxyl groups, carbonate groups, and oxygen atoms bonded to phosphorus atoms.

The invention therefore relates to a process for producing porous solid oxidic materials, comprising the provision of a hydrogel of the oxidic material, removal of the water by treatment of the hydrogel with a water-miscible liquid and drying of the organogel obtained under supercritical conditions in the presence of at least one polyfunctional compound C having at least two, for example 2, 3, 4, 5 or 6, especially 2 or 3, reactive functionalities F which can react to form a bond with the atoms of the solid oxidic material and which are selected from hydroxyl groups, especially carbon-bonded hydroxyl groups, carboxyl groups, carbonate groups, and oxygen atoms bonded to phosphorus atoms, which gives the porous solid oxidic material, the at least one polyfunctional compound C being used in the supercritical drying operation as a solution of the compound C in at least one organic solvent S' having 0 or 1 reactive functionality F, and/or as a mixture with $CO_2$.

The porous solid oxidic materials obtainable in accordance with the invention have the advantages of only low water absorption, high water resistance and high long-term stability. The polyfunctional compound C used in the process according to the invention may particularly be inexpensive compounds, for example polyhydric alcohols, hydroxycarboxylic acids, phosphates, polyphosphates and/or polycarboxylic acids.

The invention is based on the observation that polyfunctional compounds C which have at least two reactive functionalities F selected from hydroxyl groups, especially carbon-bonded hydroxyl groups, carboxyl groups, carbonate groups, and oxygen atoms bonded to phosphorus atoms, and which are present at least during the supercritical drying operation stabilize the resulting porous solid oxidic material by bond formation with the surface thereof, i.e. prevent water absorption into the porous solid oxidic material.

Preferably in accordance with the invention, the starting materials used for the production of the inventive materials are preferably inorganic hydrogels, i.e. hydrogels based on semimetal or metal oxides, particularly hydrogels based on silicon dioxide, zinc oxide, tin(IV) oxide, titanium(IV) oxide, cerium(IV) oxide and aluminum oxide, especially based on silicon dioxide. The proportion of hydrogels which are based on semimetal or metal oxides and are used with preference is generally at least 90% by weight, especially at least 95% by weight, based on the total amount of the hydrogels used.

Processes for producing hydrogels which give rise to the porous solid oxidic materials are known in principle, for example from the prior art cited at the outset. In general, the hydrogels are produced by hydrolysis of suitable metal oxide precursors, for example metal salts or covalent metal compounds or semimetal compounds such as (semi)metal halides or (semi)metal alkoxides, optionally followed by a partial condensation of the (semi)metal hydroxides or (semi)metal oxide hydroxides formed in the hydrolysis.

For example, hydrogels based on silicon dioxide are generally produced by condensation of alkali metal waterglass, especially sodium waterglass. This is typically done by mixing a waterglass solution, for example a 10 to 30 percent by weight, preferably 12 to 20 percent by weight, waterglass solution, with a dilute aqueous acid, for example a 1 to 50 percent by weight, especially 5 to 40 percent by weight, acid, especially an aqueous mineral acid, preferably sulfuric acid. Preference is given to using a sufficient amount of acid that a pH of 7.5 to 11, especially 8 to 11, more preferably 8.5 to 10, most preferably 8.5 to 9.5, is established in the mixed product. Especially suitable for this process is the use of a mixing nozzle from which the mixture of waterglass solution and dilute mineral acid is sprayed, and where the sol formed in the course of mixing solidifies in the air during the aerial phase to form hydrogel droplets. It is of course also possible, for example, to produce hydrogel moldings by combining waterglass and dilute acid in suitable form and then to allow gelation.

Prior to removal of the water, preference is given to freeing the hydrogel of ionic constituents by washing with water or dilute aqueous solutions of inorganic bases, preference being given to proceeding in such a way that the pH of the hydrogel barely changes, i.e. less than 2 pH units, especially less than 1 pH unit, and corresponds virtually to the value established in the mixed product. The inorganic bases used may, for example, be aqueous solutions of alkali metal hydroxides such as sodium hydroxide solution or aqueous ammonia. The procedure here will preferably be such that the hydrogel, even after the washing operation, has a pH within the range mentioned of 7.5 to 11, preferably 8.5 to 10, more preferably 9 to 10. The washing operation is preferably conducted until the conductivity of the washing water flowing away is about 20 to 300 µS/cm, preferably 50 to 150 µS/cm. This corresponds to an alkali metal (sodium) content of the hydrogel of generally 0.1 to 1.7% by weight, preferably 0.4 to 1.3% by weight, determined on a sample dried at 80° C. in a water jet vacuum.

The hydrogels produced in accordance with the invention may also, as described in DE 3914850, contain pigments, in which case suitable pigments are especially those which scatter, absorb or reflect infrared radiation of wavelength 3 to 10 µm. Such pigments are generally added to the hydrogel at an early stage, in the course of production thereof.

According to the invention, the water is removed from the hydrogel by treatment with a water-miscible organic liquid. The water-miscible organic liquid used for removal of the water is essentially anhydrous, i.e. it generally has a water content of not more than 5% by weight, particularly 0 to 2% by weight and especially 0 to 1% by weight, based on the overall water-miscible liquid.

The treatment of the hydrogel with the water-miscible organic liquid substantially or especially virtually completely replaces the aqueous phase present in the hydrogel with the substantially or essentially anhydrous water-miscible organic liquid. For treatment of the hydrogel with the water-miscible organic liquid, the hydrogel is contacted with the liquid, and then the treated product is separated from the liquid. For example, the hydrogel can be suspended in the water-miscible organic liquid and then the solid or gel constituents can be separated from the liquid phase, for example by filtration or centrifugation. Advantageously, the treatment is undertaken with the aid of a flow apparatus. For this purpose, the hydrogel is introduced into a suitable vessel having an inlet for the water-miscible organic liquid and an outlet, the inlet and outlet being arranged such that the water-miscible organic liquid flows through the hydrogel. The water-miscible organic liquid is fed in through the inlet, and the mixture of the water-miscible organic liquid and water is drawn off via the outlet. The treatment is preferably conducted until the water content of the organic phase flowing away is less than 2% by volume, preferably less than 1% by volume.

The temperature at which the treatment is undertaken is typically in the range from 0 to 60° C., preferably in the range from 10 to 50° C., for example 20 to 30° C. The treatment of the hydrogel with the anhydrous water-miscible organic liquid can, however, also be conducted at elevated temperature.

The removal of the water by treatment with the water-miscible organic liquid is preferably effected under subcritical conditions. Preference is given to removing the water under ambient pressure. Another possibility is exchange under reduced pressure or under elevated pressure. Typically, the treatment of the hydrogel with the water-miscible organic liquid is effected at ambient pressure.

As a result of the water exchange in the hydrogel, what is called an organogel is obtained, in which the physically bound water has substantially been exchanged for the constituents of the water-miscible organic liquid.

According to the invention, the organic liquid used for treatment of the hydrogel is water-miscible, i.e. the liquid at 20° C. has no miscibility gap with water. Preference is given to liquids which have a boiling point at standard pressure in the range from 10 to 100° C., especially in the range from 10 to 90° C. The water-miscible organic liquid is preferably an organic solvent S or a mixture of organic solvents S consisting to an extent of at least 70% by weight, based on the total amount of the water-miscible organic liquid, of one or more organic solvents S which at 20° C. have no miscibility gap with water. As well as the organic solvent S, the water-miscible organic liquid may also comprise one or more organic solvents which are immiscible or incompletely miscible with water, for example $C_2$-$C_8$-alkanes such as ethane, propane, butane, isobutane, pentane, isopentane, n-hexane and its isomers, n-heptane and its isomers, and n-octane and its isomers. As well as the organic solvent S, the water-miscible organic liquid may also comprise the compound C.

Preference is given to organic solvents S which have a boiling point at standard pressure in the range from 30 to 120° C., especially in the range from 30 to 100° C. The organic solvent S is preferably selected from $C_1$-$C_4$-alkanols, for example methanol, ethanol, n-propanol, isopropanol, n-butanol, isobutanol, 2-butanol and tert-butanol, $C_1$-$C_4$-alkanals such as formaldehyde, acetaldehyde, propionaldehyde, butyraldehyde and isobutyraldehyde, and $C_3$-$C_4$-ketones such as acetone or methyl ethyl ketone, and mixtures thereof. The organic solvent S is more preferably a $C_1$-$C_4$-alkanol. It is most preferably isopropanol.

The water-miscible organic liquid which is used in the removal of the water from the hydrogel may already comprise the polyfunctional compound C as defined below. Preferably, when the water is removed from the hydrogel, the organic solvent S is used without addition of the polyfunctional compound C The organogel is dried under supercritical conditions in the presence of the polyfunctional compound C. The polyfunctional compound C can be used either as a mixture with $CO_2$ or as a solution in an organic solvent S' which, unlike the compound C, has at most one or no functionality F. It is equally possible to use the polyfunctional compound C in a mixture of $CO_2$ and solvent S'. Preferably, either a mixture of the compound C with $CO_2$ or a solution of the compound C in an organic solvent S' is used in the supercritical drying operation.

The concentration of the polyfunctional compound C in the organic solvent S' and/or $CO_2$ is generally selected such that the resulting mixture can be converted readily to the supercritical state.

In general, the concentration of the polyfunctional compound C in the solution in the solvent S' and/or in $CO_2$ is therefore in the range from 0.01 to 50% by weight, especially in the range from 0.1 to 20% by weight, based on the overall solution and/or $CO_2$. Accordingly, the polyfunctional compound C is used generally in an amount in the range from 0.01 to 50% by weight, especially in the range from 0.1 to 20% by weight, based on the total amount of solvent S' and/or $CO_2$ and polyfunctional compound C.

According to the invention, the polyfunctional compound C has at least two, for example 2 to 10 or 2 to 5, reactive functionalities F. The compound C preferably has two or three reactive functionalities F. Reactive functionalities F are understood in the context of the invention to mean atoms and/or atom groups which can react with the atoms of the solid oxidic material to form a chemical bond, preferably a covalent chemical bond.

According to the invention, the reactive functionalities F are selected from hydroxyl groups, carboxyl groups, carbonate groups, and oxygen atoms bonded to phosphorus atoms. More particularly, the reactive functionalities F are selected from carbon-bonded hydroxyl groups, carboxyl groups and carbonate groups. More preferably, the reactive functionalities F are selected from carbon-bonded hydroxyl groups and carbonate groups.

The reactive functionalities F are preferably selected from hydroxyl groups, carboxyl groups, carbonate groups, silicon-bonded halogen atoms, silicon-bonded $C_1$-$C_4$-alkoxy groups, silicon-bonded trialkylsiloxane groups, and oxygen atoms bonded to phosphorus atoms. More particularly, the reactive functionalities F are selected from hydroxyl groups and silicon-bonded $C_1$-$C_4$-alkoxy groups.

Examples of suitable compounds C are $C_2$-$C_6$-alkanepolycarboxylic acids, i.e. polybasic, e.g. di- or tribasic, linear or branched alkanecarboxylic acid having two to six carbon atoms. Examples are oxalic acid, malonic acid, succinic acid, glutaric acid, adipic acid and maleic acid;

hydroxy-$C_2$-$C_6$-alkanemono- and -polycarboxylic acids, i.e. mono- or polybasic, e.g. mono-, di- or tribasic, linear or branched alkanecarboxylic acid having two to six carbon atoms, which have at least one hydroxyl group in addition to at least one carboxyl group. Examples are lactic acid, 2-hydroxybutanoic acid and citric acid;

$C_2$-$C_6$-alkanepolyols, e.g. di- or trihydric, linear or branched aliphatic alcohols having two to six carbon atoms. Examples are ethylene glycol, 1,2-propanediol, 1,3-propanediol, neopentyl glycol and glycerol;

$C_3$-$C_6$-cycloalkanepolyols, i.e. polyhydric, e.g. di- or trihydric, cycloaliphatic alcohols having three to six carbon atoms, such as 1,2-cyclopropanediol, 1,2-cyclopentanediol and 1,2-cyclohexanediol;

2-hydroxyphenol (catechol) and mono- and di-$C_1$-$C_4$-alkyl-2-hydroxyphenols, especially mono- and dimethyl-2-hydroxyphenols;

$C_2$-$C_4$-alkylene carbonates, i.e. cyclic esters of carbonic acid with $C_2$-$C_4$-alkanediols, e.g. ethylene carbonate (1,3-dioxolan-2-one) and propylene carbonate (4-methyl-1,3-dioxolan-2-one);

phosphates, polyphosphates, $C_1$-$C_8$-alkyl mono- and polyphosphates;

and mixtures thereof.

Preferred compounds C are 2-hydroxyphenol, $C_1$-$C_4$-alkyl-2-hydroxyphenols, $C_2$-$C_6$-alkanepolyols, especially ethylene glycol, 1,3-propanediol or 1,2-propanediol, hydroxy-$C_2$-$C_6$-alkanemono- and -polycarboxylic acids, especially lactic acid and citric acid, $C_2$-$C_4$-alkylene carbonates, especially ethylene carbonate or propylene carbonate and $C_2$-$C_6$-alkanepolycarboxylic acids, especially malonic acid or oxalic acid.

Particularly preferred compounds C are ethylene glycol, 1,2-propanediol, 1,3-propanediol, 2-hydroxyphenyl, ethylene carbonate, propylene carbonate and mixtures thereof.

Suitable solvents S' are the aforementioned water-miscible solvents S, and also $C_2$-$C_8$-alkanes and mixtures thereof. Preferred solvents S' are the aforementioned $C_1$-$C_4$-alkanols, especially isopropanol. Preferred solvents S' are additionally mixtures of the aforementioned $C_1$-$C_4$-alkanols, especially isopropanol, with $C_2$-$C_8$-alkanes.

Supercritical drying can be undertaken in a customary manner, for example in analogy to the prior art cited at the outset.

In general, the organogel and the solution of the compound C in the solvent S' and/or $CO_2$ is heated to a temperature above the critical temperature under pressure.

The drying of the organogel under supercritical conditions is effected preferably at a temperature of not more than 40 K, especially not more than 20 K, above the critical temperature of the solvent S', or not more than 50 K, particularly not more than 30 K, especially not more than 20 K, above the critical temperature of $CO_2$.

In general, the temperature is in the range from 100 to 300° C., preferably 150 to 280° C. The pressure required for this is typically in the range from 30 to 90 bar, preferably 40 to 70 bar.

If the supercritical drying takes place, for example, with isopropanol as the solvent S', a temperature of about 240 to 270° C. and a pressure of about 50 to 70 bar are generally established.

According to the invention, the drying under supercritical conditions is effected in the presence of at least one polyfunctional compound C present either as a solution in the organic solvent S', as defined above, and/or in $CO_2$. If the compound C is not already present in a sufficient amount in the essentially anhydrous water-miscible organic liquid used in the water exchange, the compound C is added to the organogel, preferably as a solution in the solvent S'.

For drying, the mixture of organogel, the compound C and the solvent S' or $CO_2$ is typically introduced into a pressure vessel and the mixture is brought under supercritical conditions. For this purpose, the closed pressure vessel, for example an autoclave, is preferably heated with limitation of the pressure to a supercritical temperature. The mixture is preferably kept under supercritical conditions for 1 min to 8 h, especially 1 min to 4 h.

The solvent S' and/or $CO_2$ is then removed from the pressure vessel by decompression, preferably isothermal decompression, preferably gradually by gently opening the pressure valve. Preference is given to conducting the decompression at a decompression rate in the range from 0.1 to 5 bar/min.

During the supercritical drying operation, the formation of any great volumes of gas through uncontrolled vaporization or outgassing will preferably be prevented by means of decompression, i.e. said removal of the gas mixture via the pressure valve.

The supercritical drying step may be followed by further purification and workup steps. These may, for example, be the purging of the pressure vessel with compressed air or gaseous nitrogen, in order particularly to remove residues of the solvent S' still present. The supercritical drying step may also be followed by a subcritical, conventional drying operation at slightly elevated temperature, optionally while purging with compressed air or gaseous nitrogen.

The process product obtained from the process according to the invention is a porous solid oxidic material which, owing to the treatment with the compound C, has improved properties, especially a hydrophobized surface and lower water absorption, even in the case of prolonged water contact.

Owing to the high porosity, the material has only low bulk densities of about 25 to 300 g/L, especially 50 to 250 g/L. The proportion of pores in the total volume of the material is about 50 to 97% by volume.

In preferred embodiments of the invention, the porous solid oxidic material obtainable in accordance with the invention comprises, as the main component, i.e. in an amount of 90 to 100% by weight, based on the total weight of the oxidic material, at least one oxide from the group of silicon dioxide, zinc oxide, tin(IV) oxide, titanium(IV) oxide, cerium(IV) oxide and aluminum oxide. More particularly, the porous solid oxidic material obtainable in accordance with the invention comprises, as the main component, i.e. in an amount of 90 to 100% by weight, based on the total weight of the oxidic material, at least one oxide from the group of silicon dioxide, titanium(IV) oxide and aluminum oxide or a mixture of these oxides with at least one further oxide from the group of zinc oxide, tin(IV) oxide and cerium(IV) oxide. Specifically, the solid oxidic material comprises, as the main component, i.e. in an amount of 90 to 100% by weight, based on the total weight of the oxidic material, at least one oxide from the group of silicon dioxide.

The porous solid oxidic material is preferably an aerogel. The porous solid oxidic material is more preferably an aerogel based on silicon dioxide.

The porous solid oxidic material obtained in accordance with the invention can be used either in the form of granules (typical particle sizes from 1 to 8 mm) or after prior grinding or the like as powder (particle sizes of less than 1 mm) for different purposes, for example as described in the introduction.

The porous solid oxidic material obtainable by the process according to the invention generally has a density in the range from 0.025 to 0.25 $g/cm^3$.

The inventive materials are suitable for a multitude of applications.

The examples which follow serve to illustrate the invention.

EXAMPLES

Chemicals Used:
isopropanol (99.9%, from BCD Chemie)
ethylene glycol (99.8%, from Sigma-Aldrich)
1,2-propanediol (99%, from Sigma-Aldrich)
1,3-propanediol (99%, from Sigma-Aldrich)
2-hydroxyphenol (99%, from Sigma-Aldrich)
ethylene carbonate (99%, from Sigma-Aldrich)
propylene carbonate (99%, from Sigma-Aldrich)
1-propanol (99%, from Sigma-Aldrich)
ethanol (anhydrous, 99%, from Sigma-Aldrich)

Analysis:
Bulk density based on ISO 3944
Specific surface area by adsorption of nitrogen according to BET at a temperature of −196° C. to DIN ISO 9277
Elemental analysis (determination of the carbon content of the samples as a measure of the success of the surface reaction): vario MICRO cube (from Elementar, CHN operating mode at 1000° C.)
Contact angle measurements to DIN 55660
Water absorption: measurement of the increase in weight of the samples after storage at 23° C. and >90% relative humidity for 24 h
Water resistance: The material to be examined was ground in a mortar to a powder.

About 5 mL of water were introduced into a closable 10 mL glass vessel and a sufficient amount of powder was added to the glass vessel that the powder covered the entire surface of the water. Because of its low density, the powder floated on the surface of the water. The powder volume required for the full surface coverage of the water in the glass vessel was about 1 mL. The glass vessel was closed and stored at room temperature, and the time until the floating powder started to fall to the base of the glass vessel was measured. The longer the powder remained completely on the surface of the water, the more hydrolysis-resistant was the hydrophobic surface modification of the material examined.

PREPARATION EXAMPLES

Preparation of a Hydrogel Based on Silica

A 13% by weight waterglass solution was prepared by diluting a technical waterglass solution comprising 27% by weight of silicon dioxide and 8% by weight of sodium oxide with water.

In a mixing nozzle, at 20° C. and 2.5 bar, 45.7 L/h of the 13% by weight waterglass solution prepared were combined with 6 L/h of a 23% by weight aqueous sulfuric acid solution. The unstable hydrosol which formed as a result of progressive neutralization of the waterglass solution in the mixing chamber had a pH of 8.1±0.1 and, after a residence time of 0.1 s, was sprayed through the nozzle mouth (diameter 2 mm). As it flew through the air, the liquid jet separated into individual droplets, which solidified to give transparent, mechanically stable hydrogel spheres before hitting the water basin.

The hydrogel obtained in this way was washed with demineralized water until the wash liquid flowing away had an electrical conductivity of less than 110 µS/cm and a pH of 9.8±0.1. The sodium content of a sample of the hydrogel dried at 80° C. in a water jet vacuum was 1.1% by weight.

Preparation of the Alcogel (Isopropanol)

2000 g of the hydrogel based on silica were introduced into a 5 L vessel, which was filled completely with isopropanol. At 25° C., anhydrous isopropanol was pumped through the vessel until the water content of the isopropanol flowing away was less than 0.1% by volume. This required about 8 L of isopropanol.

Supercritical drying of the alcogel based on isopropanol (general method):

2 L of the alcogel together with 4 L of isopropanol and 40 mL of the compound C were introduced into a heatable stainless steel (RA4) pressure vessel having a capacity of 20 L and the mixture was heated to 270° C. within 5 h, in the course of which the pressure in the pressure vessel was limited to 70 bar. This was followed by isothermal decompression within 60 min. The cooled reaction product was withdrawn and subjected to further drying at 80° C. and 200 mbar for approx. 2 h.

Example 1

Ethylene Glycol

The starting material was the above-described alcogel based on isopropanol. For supercritical drying, the compound C used was ethylene glycol.

The bulk density of the resulting aerogel was 110 g/L. The specific surface area was 300 m$^2$/g. The carbon content was 5.8% by weight. The surface was hydrophobic and had a contact angle with respect to water of 155°. The water absorption was 1.1% by weight. The water resistance was about 12 to 14 days.

The surface of the aerogel was examined by means of solid state $^{13}$C NMR. This gave two different carbon signals which are attributable firstly to the two chemically equivalent carbon atoms of ethylene glycol, and secondly to the oxygen-bonded carbon atom of isopropanol. The intensity ratio of the signals between doubly bonded ethylene glycol molecules and singly bonded isopropanol molecules was about 3:1.

Example 2

1,2-propanediol

The starting material was the above-described alcogel based on isopropanol. For supercritical drying, the compound C used was 1,2-propanediol.

The bulk density of the resulting aerogel was 112 g/L. The specific surface area was 310 m$^2$/g. The carbon content was 5.9% by weight. The surface was hydrophobic and had a contact angle with respect to water of approx. 140°. The water absorption was 1.8% by weight. The water resistance was about 8 days.

Example 3

1,3-propanediol

The starting material was the above-described alcogel based on isopropanol. For supercritical drying, the compound C used was 1,3-propanediol.

The bulk density of the resulting aerogel was 120 g/L. The specific surface area was 310 m$^2$/g. The carbon content was 6.2% by weight. The surface was hydrophobic and had a contact angle with respect to water of approx. 145°. The water absorption was 1.9% by weight. The water resistance was about 6 days.

Example 4

2-hydroxyphenol

The starting material was the above-described alcogel based on isopropanol. For supercritical drying, the compound C used was 2-hydroxyphenol.

The bulk density of the resulting aerogel was 110 g/L. The specific surface area was 340 m$^2$/g. The carbon content was 6.5% by weight. The surface was hydrophobic and had a contact angle with respect to water of approx. 155°. The water absorption was 1.0% by weight. The water resistance was more than 14 days.

Example 5

Ethylene Carbonate

The starting material was the above-described alcogel based on isopropanol. For supercritical drying, the compound C used was ethylene carbonate.

The bulk density of the resulting aerogel was 120 g/L. The specific surface area was 320 m$^2$/g. The carbon content was 6% by weight. The surface was hydrophobic and had a contact angle with respect to water of approx. 150°. The water absorption was 1.2% by weight. The water resistance was about 10 days.

Comparative Example 1

Isopropanol

The starting material was the above-described alcogel based on isopropanol. For supercritical drying, instead of a mixture of isopropanol and compound C, exclusively isopropanol was used.

The bulk density of the resulting aerogel was 115 g/L. The specific surface area was 330 m$^2$/g. The carbon content was 6.0% by weight. The surface was hydrophobic and had a contact angle with respect to water between 120 and 140°. The water absorption was 2.1% by weight. The water resistance was about 12 to 24 h.

Comparative Example 2

1-propanol

The starting material was the above-described alcogel based on isopropanol. For supercritical drying, rather than a mixture of isopropanol and compound C, exclusively 1-propanol was used.

The bulk density of the resulting aerogel was 125 g/L. The specific surface area was 320 m$^2$/g. The carbon content was 5.8% by weight. The surface was hydrophobic and had a contact angle with respect to water between 120 and 140°. The water absorption was 2.0% by weight. The water resistance was about 18 h.

Comparative Example 3

Ethanol

The starting material was the above-described alcogel based on isopropanol. For supercritical drying, rather than a mixture of isopropanol and compound C, exclusively ethanol was used.

The bulk density of the resulting aerogel was 125 g/L. The specific surface area was 300 m$^2$/g. The carbon content was 5% by weight. The surface was hydrophobic and had a contact angle with respect to water between 120 and 130°. The water absorption was 2.2% by weight. The water resistance was about 8 to 12 h.

The invention claimed is:

1. A process for producing porous solid oxidic materials in which the porous solid oxidic materials are aerogels, comprising
   providing an inorganic hydrogel of the oxidic material;
   removing water from the inorganic hydrogel by treatment with a water-miscible organic liquid to obtain an organogel;
   and drying the organogel obtained under supercritical conditions in the presence of at least one polyfunctional compound C;
   wherein the at least one polyfunctional compound C comprises at least two reactive functionalities F selected from the group consisting of hydroxyl groups, carboxyl groups, carbonate groups, oxygen atoms bonded to phosphorus atoms, and combinations thereof;
   wherein each of the at least two reactive functionalities F reacts to form a bond with the atoms of the organogel to form the aerogel;
   wherein the at least one polyfunctional compound C is selected from the group consisting of hydroxy-$C_2$-$C_6$-alkanemono- and -polycarboxylic acids, $C_2$-$C_6$-alkanepolyols, $C_3$-$C_6$-cycloalkanepolyols, 2-hydroxyphenol, mono- and di-$C_1$-$C_4$-alkyl-2-hydroxyphenols, $C_2$-$C_4$-alkylene carbonates, phosphates, polyphosphates, $C_1$-$C_8$-alkyl mono- and polyphosphates and mixtures thereof, and is present in the supercritical drying operation as a solution of the compound C in at least one organic solvent S' having 0 or 1 reactive functionality F, and/or as a mixture with $CO_2$;
   wherein the amount of polyfunctional compound C, based on the total amount of solvent S' or $CO_2$ and polyfunctional compound C, is in the range from 0.01 to 50% by weight; and
   wherein the organic solvent S' at standard pressure has a boiling point in the range from 10 to 120° C.

2. The process according to claim 1, wherein the oxidic material comprises, as the main component, at least one oxide from the group consisting of silicon dioxide, zinc oxide, tin(IV) oxide, titanium(IV) oxide, cerium(IV) oxide and aluminum oxide in an amount of 90 to 100% by weight, based on the total weight of the oxidic material.

3. The process according to claim 1, wherein the hydrogel is a hydrogel based on silicon dioxide.

4. The process according to claim 1, wherein the compound C has two or three reactive functionalities F.

5. The process according to claim 1, wherein the reactive functionalities F are selected from the group consisting of carbon-bonded hydroxyl groups, carboxyl groups and carbonate groups.

6. The process according to claim 1, wherein the compound C is selected from the group consisting of $C_2$-$C_6$-alkanepolyols, $C_2$-$C_4$-alkylene carbonates and 2-hydroxyphenol.

7. The process according to claim 1, wherein the compound C is selected from the group consisting of ethylene glycol, 1,2-propanediol, 1,3-propanediol, 2-hydroxyphenol, ethylene carbonate and propylene carbonate.

8. The process according to claim 1, wherein the organic solvent S' at standard pressure has a boiling point in the range from 10 to 100° C.

9. The process according to claim 1, wherein the organic solvent S' is selected from the group consisting of $C_1$-$C_4$-alkanols, $C_2$-$C_8$-alkanes, $C_1$-$C_4$-alkanals, $C_3$-$C_4$ ketones and mixtures thereof.

10. The process according to claim 1, wherein the organic solvent S' is isopropanol.

11. The process according to claim 1, wherein removal of the water is preceded by freeing the hydrogel of ionic constituents by washing with water or dilute aqueous solutions of inorganic bases.

12. The process according to claim 1, wherein the water is removed by treating the hydrogel with a water-miscible organic liquid under subcritical conditions.

13. The process according to claim 12, wherein the water-miscible organic liquid has a water content of not more than 5% by weight.

14. The process according to claim 1, wherein the drying under supercritical conditions is effected at a temperature of not more than 20° C. above the critical temperature of the water-miscible organic liquid.

15. The process according to claim 1, wherein the amount of polyfunctional compound C, based on the total amount of solvent S' or $CO_2$ and polyfunctional compound C, is in the range from 0.1 to 20% by weight.

16. The process according to claim 1, wherein the compound C is selected from the group consisting of $C_2$-$C_6$-alkanepolyols, $C_2$-$C_4$-alkylene carbonates and 2-hydroxyphenol and the organic solvent S' is selected from the group consisting of $C_1$-$C_4$-alkanols, $C_2$-$C_8$-alkanes, $C_1$-$C_4$-alkanals, $C_3$-$C_4$ ketones and mixtures thereof.

17. The process according to claim 1, wherein the compound C is selected from the group consisting of ethylene glycol, 1,2-propanediol, 1,3-propanediol, 2-hydroxyphenol, ethylene carbonate and propylene carbonate and the organic solvent S' is selected from the group consisting of $C_1$-$C_4$-alkanols, $C_2$-$C_8$-alkanes, $C_1$-$C_4$-alkanals, $C_3$-$C_4$ ketones and mixtures thereof.

* * * * *